United States Patent
Sadasivan Vijayakumari et al.

(10) Patent No.: US 8,785,703 B2
(45) Date of Patent: *Jul. 22, 2014

(54) PROCESS FOR PREPARING ETHYLENE AND PROPYLENE

(75) Inventors: Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,232

(22) Filed: Sep. 7, 2012

(65) Prior Publication Data

US 2013/0245291 A1    Sep. 19, 2013

(30) Foreign Application Priority Data

Sep. 7, 2011  (EP) .................................... 11180320

(51) Int. Cl.
*C07C 2/00*  (2006.01)

(52) U.S. Cl.
USPC ........... 585/326; 585/324; 585/640; 549/513; 549/523

(58) Field of Classification Search
USPC ........... 585/324, 326, 639, 640; 549/513, 523
See application file for complete search history.

(56) References Cited

U.S. PATENT DOCUMENTS

| | | | |
|---|---|---|---|
| 4,567,029 A | 1/1986 | Wilson et al. | |
| 6,049,017 A | 4/2000 | Vora et al. | |
| 6,235,954 B1 * | 5/2001 | Wu et al. | 585/260 |
| 7,238,846 B2 * | 7/2007 | Janssen et al. | 585/640 |
| 7,402,718 B2 * | 7/2008 | Janssen et al. | 585/638 |
| 7,642,294 B2 * | 1/2010 | Cruijsberg et al. | 518/700 |
| 7,932,427 B2 * | 4/2011 | Chewter et al. | 585/651 |
| 8,049,054 B2 * | 11/2011 | Chewter et al. | 585/643 |
| 8,269,056 B2 * | 9/2012 | Van Westrenen et al. | 585/639 |
| 8,507,742 B2 * | 8/2013 | Chewter et al. | 585/324 |
| 2007/0155999 A1 | 7/2007 | Pujado et al. | |
| 2007/0203380 A1 | 8/2007 | Vora et al. | |

FOREIGN PATENT DOCUMENTS

| | | |
|---|---|---|
| WO | 2006020083 | 2/2006 |
| WO | 2009156433 | 12/2009 |

OTHER PUBLICATIONS

Hamid, et al.; Handbook of MTBE and Other Gasoline Oxygenates; 1st edition, pp. 65 to 223; 2004.

* cited by examiner

*Primary Examiner* — Golam M M Shameem

(57) ABSTRACT

The present invention provides a process for preparing ethylene and/or propylene, comprising the steps of contacting a stream comprising C4+ olefins with a zeolite-comprising catalyst at a temperature in the range of from 350 to 1000° C. and retrieving an olefinic product stream comprising:

ethylene and/or propylene, and a C4+ hydrocarbon fraction, comprising paraffins, normal olefins and iso-olefins;

The C4+ hydrocarbon fraction is recycled while part of the fraction is purged. The part of the C4+ hydrocarbon with is purged is treated to extract C4+ isoolefins as tert-alkyl ethers. At least part of tert-alkyl ethers are converted to further ethylene and propylene.

14 Claims, 1 Drawing Sheet

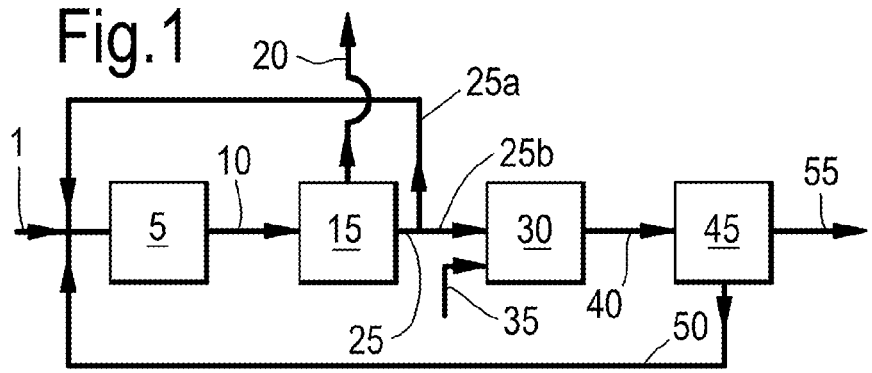
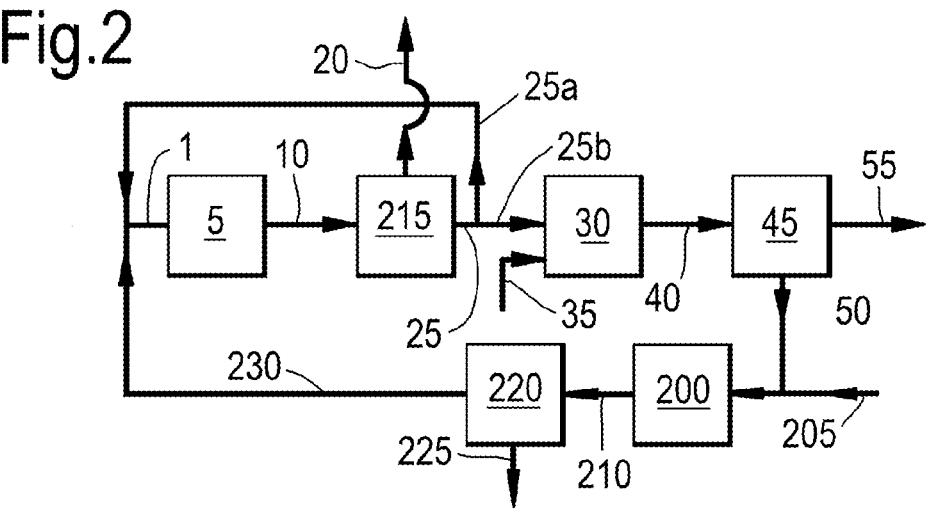
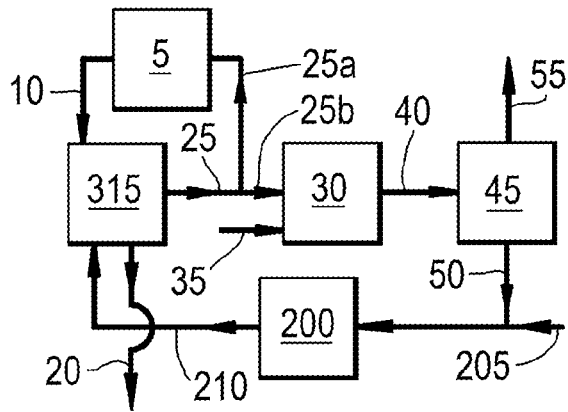

PROCESS FOR PREPARING ETHYLENE AND PROPYLENE

This application claims the benefit of European Application No. 11180320.1 filed Sep. 7, 2011, which is incorporated herein by reference.

FIELD OF THE INVENTION

The invention relates to a process for preparing ethylene and/or propylene.

BACKGROUND TO THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance to methanol or dimethylether (DME), both of which are suitable feedstocks for an OTO process.

In an OTO process, an oxygenate such as methanol is provided to a reaction zone comprising a suitable conversion catalyst and converted to ethylene and propylene. In addition to the desired ethylene and propylene, a substantial part of the methanol is converted to higher hydrocarbons including C4+ olefins and paraffins. In order to increase the ethylene and propylene yield of the process, the C4+ olefins may be recycled to the reaction zone or alternatively further cracked in a dedicated olefin cracking zone to produce further ethylene and propylene. In WO2009/156433, process is described, wherein an oxygenate feedstock is converted in an OTO zone (XTO zone) to an ethylene and propylene product. Higher olefins, i.e. C4+ olefins, produced in the OTO zone are directed to an olefin cracking zone (OC zone). In the olefin cracking zone, part of the higher olefins are converted to additional ethylene and propylene, however substantial amounts of higher olefins remain in the effluent of the olefin cracking zone. After separating the ethylene and propylene from the effluent of the olefin cracking zone, the remaining effluent of the olefin cracking zone is recycled and fed to the inlet of the olefin cracking zone together with the higher olefins stream from the OTO zone. A problem encountered with the process described in WO2009/156433, is the build-up of C4+ paraffins in the recycle to the olefin cracking zone. Paraffins are produced as a side product in the OTO reaction and accumulate in the bottom stream of the depropaniser together with the C4+ olefin fraction during the work-up of both the OTO zone as the olefin cracking zone effluent. The C4+ paraffins are not converted in the olefin cracking zone and therefore remain in the recycle. Due to the small differences in boiling temperature of the olefins and corresponding paraffins, the C4+ paraffins are difficult to separate from the C4+ olefin fraction recycle. To maintain acceptable levels of paraffins in the C4+ olefin fraction recycle it is therefore necessary to withdraw part of the C4+ olefin fraction recycle to the olefin cracking zone as a purge stream. Consequently, part of the valuable C4+ olefins are lost as part of the purge stream.

In U.S. Pat. No. 6,049,017, a similar process is described, wherein an oxygenate feedstock is converted in an OTO zone over a SAPO-34 catalyst to an effluent comprising ethylene, propylene, butylenes and paraffins. A stream comprising butylenes and paraffins is separated from the OTO zone effluent and directed to a butylenes cracking zone, wherein butylenes are cracked over a SAPO-34 catalyst. The cracked effluent of the butylenes cracking zone is combined with the effluent of the OTO zone, thereby allowing any remaining butylenes in the cracked effluent to be recycled to the butylenes cracking zone. Also in the process of U.S. Pat. No. 6,049,017, a paraffin content is built-up in the butylenes recycle. Therefore, a purge stream (drag stream) is withdrawn from the process prior to feeding the stream comprising butylenes and paraffins to the butylenes cracking zone. To prevent the loss of butenes in the purge stream, the purge stream is provided to an oligomerisation reactor, wherein n-butenes undergo oligomerisation to higher olefins, i.e. C8, C12, c16 and higher olefins. These higher olefins are subsequently separated from the paraffins in the purge stream and directed to the butylenes cracking zone. A disadvantage of the process of U.S. Pat. No. 6,049,017 is that the cracking of the higher olefins oligomerisation product results in the increased formation of paraffins and aromatics in the butylenes cracking zone. In addition, the cracking of higher olefins in a butylenes cracking zone is much more prone to coke formation resulting in increased catalyst deactivation. Furthermore, the oligomerisation only provides capture of n-butylenes in the purge stream, iso-olefins are not captured, but purged from the process. Consequently, a less than optimal ethylene and propylene yield is achieved.

SUMMARY OF THE INVENTION

There is a need in the art for a process allowing for an improved utilization of C4+ olefins in a process for producing ethylene and propylene.

It has now been found that by reacting iso-olefins in purge stream of a process for producing ethylene and propylene with methanol into a tert-alkyl ether, the utilization of C4+ olefins can be improved by converting the tert-alkyl ether into further ethylene and propylene.

Accordingly, the present invention provides process for preparing ethylene and/or propylene, comprising the steps of
a) contacting a stream comprising C4+ olefins with a zeolite-comprising catalyst at a temperature in the range of from 350 to 1000° C. and retrieving an olefinic product stream comprising:
  ethylene and/or propylene, and
  a C4+ hydrocarbon fraction, comprising paraffins, normal olefins and iso-olefins;
b) recycling a first part of the C4+ hydrocarbon fraction to step (a).
c) subjecting a second part of the C4+ hydrocarbon fraction to an etherification process with methanol and/or ethanol wherein at least part of the iso-olefins are converted with methanol and/or ethanol to an tert-alkyl ether, and retrieving an etherification product stream;
d) separating at least part of the etherification product stream into at least an ether-enriched stream and an iso-olefin-depleted C4+ hydrocarbon stream;
e) withdrawing at least part of the iso-olefin-depleted C4+ hydrocarbon stream from the process to purge part of the paraffinic C4+ hydrocarbons;
f) converting at least part of the tert-alkyl ether in the ether-enriched stream to ethylene and/or propylene by contacting at least part of the ether-enriched stream with a molecular sieve-comprising catalyst at a temperature in the range of from 350 to 1000° C.

By extracting iso-olefins from the purge stream of a process to produce ethylene and propylene in the form of tert-alkyl ether, additional ethylene and/or propylene may be produced either by recycling the tert-alkyl ether back to step (a)

of the process to produce ethylene and propylene together with the remaining C4+ olefins or by separately converting the tert-alkyl ether to ethylene and propylene in for example an oxygenate-to-olefins (OTO) process.

An advantage of extracting the iso-olefins from the purge stream and not from the entire C4+ hydrocarbon fraction is that a much smaller etherification unit is required.

BRIEF DESCRIPTION OF THE DRAWINGS

FIG. 1 provides a schematic representation of a process according to the invention.

FIG. 2 provides a schematic representation of another process according to the invention.

FIG. 3 provides a schematic representation of a further process according to the invention.

DETAILED DESCRIPTION OF THE INVENTION

Ethylene and propylene can be produced from C4+ olefins, in particular C4 and C5 olefins, by contacting a stream comprising C4+ olefins with a zeolite-comprising catalyst at elevated temperatures. The effluent of such a conversion process typically comprises the desired ethylene and/or propylene, but also comprises a C4+ hydrocarbon fraction, which comprises further olefins, either non reacted or newly formed, and paraffins. This C4+ hydrocarbon fraction is typically recycled to be part of the feed to the conversion process. The paraffins in the C4+ hydrocarbon fraction are also recycled, but are not converted. Consequently, paraffin levels in the feed to the process increase as C4+ hydrocarbon fraction is continuously recycled. In order to maintain acceptable levels of paraffins in the feed to the process, part of the C4+ hydrocarbon fraction is withdrawn from the process as a purge stream. As it is difficult to separate olefins from their corresponding paraffins, inevitably also part of the valuable olefins are lost when purging part of the C4+ fraction.

In the process according to the present invention, measures are provided to reduce the amount of valuable olefins that are lost with the paraffin purge. In the process according to the invention, iso-olefins are extracted from the purge stream, prior to withdrawing the purge stream from the process. The iso-olefins are extracted by reacting the iso-olefins with methanol and/or ethanol, but preferably methanol, to form tert-alkyl ether, such as for example methyl tert-butyl ether (MTBE) or tert-amyl methyl ether (TAME). The formed ethers can be separated from the remainder of the C4+ fraction that is to be purged. Only iso-olefins, wherein the double bound is located directly adjacent to a tertiary carbon atom can react with methanol to form tert-alkyl ethers. Such iso-olefins are herein referred to as tertiary iso-olefins. Examples of such tertiary iso-olefins include isobutene, 2-methyl-1-butene and 2-methyl-2-butene. An example of an iso-olefin that is not a tertiary iso-olefin is 3-methyl-1-butene. Therefore, in the process according to the present invention at least part of the iso-olefins in the C4+ hydrocarbon fraction should be tertiary iso-olefins. By extracting the iso-olefins from the C4+ fraction to be purged, the olefin concentration in the purge stream fraction is lowered, while the paraffin concentration is increased.

The tert-alkyl ethers, obtained by extracting the iso-olefins from the C4+ hydrocarbon fraction by reacting the iso-olefins with methanol, may be used to produce further ethylene and/or propylene. As a result less olefins are lost with the paraffins in the paraffin purge.

The process according to the invention is now described in more detail herein below.

The process according to the present invention is a process for preparing ethylene and/or propylene. In the process according to the invention, a stream comprising C4+ olefins is provided. Preferably, the stream comprising C4+ olefins comprises at least C4 and/or C5 olefins, preferably at least C4 olefins. More preferably, the stream comprising C4+ olefins comprises in the range of from 10 to 100 wt % of C4 and/or C5 olefins based on the weight of the olefins in the stream comprising C4+ olefins, preferably of from 50 to 100 wt % of C4 and/or C5 olefins based on the weight of the olefins in the stream comprising C4+ olefins. Even more preferably, the stream comprising C4+ olefins comprises in the range of from 10 to 100 wt % of C4 olefins based on the weight of the olefins in the stream comprising C4+ olefins, preferably of from 50 to 100 wt % of C4 olefins based on the weight of the olefins in the stream comprising C4+ olefins. Optionally, the stream comprising C4+ olefins also contains a diluent. Examples of suitable diluents include, but are not limited to, water or steam, nitrogen, argon and methane.

The stream comprising C4+ olefins is contacted with a zeolite-comprising catalyst. Reference herein to a zeolite comprising catalyst is to a catalyst comprising at least a zeolite. The stream comprising C4+ olefins may contacted with the zeolite-comprising catalyst in a reactor.

The stream comprising C4+ olefins is contacted with the zeolite-comprising catalyst at a temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

When C4+ olefins, and in particular C4 and/or C5 olefins, are contacted with zeolites, i.e. the zeolite in the zeolite-comprising catalyst, at the prescribed temperatures the C4+ olefins are converted to at least ethylene and/or propylene, preferably ethylene and propylene. In addition to ethylene and/or propylene, also paraffins are formed, including at least C4+ paraffins.

Following the contacting of the stream comprising C4+ olefins with the catalyst an olefinic product stream can be retrieved from the reactor. The olefinic product stream comprises at least ethylene and/or propylene. Preferably, the olefinic product comprises advantageously at least 50 mol %, in particular at least 50 wt %, ethylene and propylene, based on total hydrocarbon content in the olefinic product. In addition, the olefinic product stream comprises a C4+ hydrocarbon fraction. Reference herein to a C4+ hydrocarbon is to hydrocarbons comprising 4 or more carbon atoms. Preferably, the C4+ hydrocarbon fraction comprises in the range of from 80 to 100 wt % of C4+ hydrocarbons, more preferably of 90 to 100 wt % of C4+ hydrocarbons, based on the total weight of the C4+ hydrocarbon fraction. This C4+ hydrocarbon fraction comprises paraffins, normal olefins and iso-olefins, optionally the C4+ hydrocarbon fraction also comprises diolefins. Each of the paraffins, normal olefins and iso-olefins may be unreacted paraffins, normal olefins and iso-olefins originally contained in the stream comprising C4+ olefins or may be paraffins, normal olefins and iso-olefins formed in contact with the zeolite-comprising catalyst.

Preferably, the C4+ hydrocarbon fraction comprises at least C4 and/or C5 olefins, preferably at least C4 olefins. More preferably, the C4+ hydrocarbon fraction comprises in the range of from 10 to 100 wt % of C4 and/or C5 olefins based on the weight of the olefins in the C4+ hydrocarbon fraction, preferably of from 50 to 100 wt % of C4 and/or C5 olefins based on the weight of the olefins in the C4+ hydrocarbon fraction. Even more preferably, the C4+ hydrocarbon fraction comprises in the range of from 10 to 100 wt % of C4 olefins based on the weight of the olefins in the C4+ hydrocarbon fraction, preferably of from 50 to 100 wt % of C4 olefins based on the weight of the olefins in the C4+ hydrocarbon fraction. Preferably, the C4+ hydrocarbon fraction comprises in the range of from 0 to 10 wt % of C6+ olefins, i.e. olefins comprising 6 carbon atoms or more, more preferably 0 to 5 wt % of C6+ olefins, based on the weight of the olefins in the C4+ hydrocarbon fraction. Preferably, in the range of from 1 to 60 wt % of the olefins in the C4+ hydrocarbon fraction are iso-olefins, more preferably of from 5 to 50 wt % of the olefins in the C4+ hydrocarbon fraction are iso-olefins, based on the weight of the olefins in the C4+ hydrocarbon fraction.

Preferably, the C4+ hydrocarbon fraction comprises in the range of from 1 to 60 wt %, more preferably of from 5 to 50 wt %, of paraffins, based on the weight of the hydrocarbons in the in C4+ hydrocarbon fraction.

The olefinic product stream may also comprise water or steam, methane, ethane, propane, C2 and/or C3 diolefins and any diluents as present in the stream comprising C4+ olefins.

Preferably, the C4+ hydrocarbon fraction of the olefinic product stream is separated from the remainder of the olefinic product stream prior to being subjected to the etherification process. The C4+ hydrocarbon fraction of the olefinic product stream may separated from the remainder of the olefinic product by any suitable work-up section. The olefinic product stream may be separated in a fraction comprising ethylene and/or propylene and C4+ hydrocarbon fraction. The design of the work-up section depends on the exact composition of the olefinic product stream, and may include several separation steps.

In the process according to the present invention, a first part of the C4+ hydrocarbon fraction is recycled to step (a) of the process to form part of the C4+ olefin-comprising stream.

To prevent a built-up of paraffins in the process, by continuously recycling unreacted paraffins in the C4+ hydrocarbon fraction, at least part of the C4+ hydrocarbon fraction is withdrawn from the process to purge part of the paraffinic C4+ hydrocarbons in the C4+ hydrocarbon fraction. Preferably, in the range of from 1 to 5 wt % of the C4+ hydrocarbon fraction is removed from the process as purge stream, this part of the C4+ hydrocarbon fraction is also referred to as the second part of the C4+ hydrocarbon fraction. In the process according to the invention, prior to withdrawing the second part of the C4+ hydrocarbon fraction from the process, the second part of the C4+ hydrocarbon fraction is first subjected to an etherification process.

In the etherification process the second part of the C4+ hydrocarbon fraction is contacted with methanol in the presence of a suitable etherification catalyst. When the iso-olefins in the C4+ hydrocarbon fraction are contacted with methanol in the presence of an etherification catalyst, at least part of the iso-olefins are converted with methanol to tert-alkyl ethers. Reference herein in to a tert-alkyl ether is to an ether of methanol and an iso-olefin. Examples of such tert-alkyl ethers are MTBE and TAME, which are tert-alkyl ethers of methanol and respectively isobutene and isopentene. From the etherification process, an etherification product stream is retrieved. The etherification product stream will comprise the formed tert-alkyl ethers and the remainder of the second part of the C4+ hydrocarbon fraction, i.e. the unreacted components. In addition, the etherification product stream may also comprise unreacted methanol.

At least part, and preferably all, of the etherification product stream is separated into at least an ether-enriched stream and an iso-olefin-depleted C4+ hydrocarbon stream. The separation of the etherification product stream into an ether-enriched stream and an iso-olefin-depleted C4+ hydrocarbon stream can be done with normal separation means provided in the art. Typically the etherification reaction is performed in the presence of an excess of alcohol, i.e. above reaction stoichiometry with the iso-olefin. Due to the large difference in boiling temperature between the formed ethers and the remaining components in the etherification product stream, the etherification product stream may be separated using conventional distillation columns and gas/liquid separators. It is preferred to concentrate any methanol in the ether-enriched stream. Due to the relatively high boiling point of methanol, the bulk of the excess alcohol can be directed toward the ether-enriched stream. Methanol may form an azeotropic mixture with the C4 olefins in the iso-olefin-depleted C4+ hydrocarbon stream. The methanol concentration in the azeotropic mixture is approximately 4 wt %, based on weight of the azeotropic mixture. It may be desired to remove the methanol prior to purging any part of the iso-olefin-depleted C4+ hydrocarbon stream, as methanol is a valuable feedstock for producing ethylene and propylene. Methanol may be extracted from the iso-olefin-depleted C4+ hydrocarbon stream by a water extraction. In one embodiment methanol is separated from hydrocarbons in an extraction column. Methanol and hydrocarbons are fed to the bottom part of the extractor and water to the top section. The column is typically filled with random packing or sieve trays, which enhance methanol mass-transfer from the hydrocarbon phase to the water phase. Essentially methanol-free hydrocarbons may be retrieved above the water feed point, and a water/methanol mixture is the bottom product. The methanol may separated from the water by distillation an led back to the etherification process, or, preferably the water/methanol mixture may be contacted with a molecular sieve to produce ethylene and/or propylene, for instance by providing the water/methanol mixture to an OTO unit.

The iso-olefin-depleted C4+ hydrocarbon stream is withdrawn from the process to purge part of the paraffinic C4+ hydrocarbons.

In the process according to the present invention, the ethylene and/or propylene yield is further increased by converting at least part of the tert-alkyl ethers in the ether-enriched stream to ethylene and/or propylene. At least part of the tert-alkyl ethers in the ether-enriched stream are converted by providing the ether-enriched stream to a reactor and contacting at least part of the ether-enriched stream with a molecular sieve-comprising catalyst to obtain a further olefinic product, comprising ethylene and/or propylene. In addition, the further olefinic product may also comprise a C4+ hydrocarbon fraction, which may comprise C4+ olefins. The ether-enriched stream is contacted with the molecular sieve-comprising catalyst at a temperature in the range of from 350 to 1000° C., preferably of from 350 to 750° C. When the tert-alkyl ethers, and in particular MTBE and/or TAME, are contacted with molecular sieves, i.e. the molecular sieve in the molecular sieve-comprising catalyst, the tert-alkyl ethers are at least partially converted to at least ethylene and/or propylene, preferably ethylene and propylene. In addition to ethylene and/or propylene, also C4+ olefins may be formed. As the tert-alkyl ethers are oxygenates, the conversion of the tert-alkyl ethers in the ether-enriched stream may be considered as an OTO process and operated as such an OTO process. Process conditions for operating an OTO process are provided herein below.

The conversion of oxygenates, such as methanol and DME, under such conditions to olefins in the presence of molecular sieve-comprising catalysts is well known in the art. With respect to the tert-alkyl ethers it is believed, without wishing to be bound to a particular theory, that upon contacting the molecular sieve-catalyst, the tert-alkyl ether decomposes into its corresponding alcohol, i.e. methanol, and iso-olefin, e.g. isobutene or isopentene. This decomposition reaction is acid-catalysed. Therefore, preferably the molecular sieve-comprising catalyst comprises acid groups. Some molecular sieves are acidic by nature, whereas other molecular sieve-comprising catalysts comprise binder, support, matrix or other materials comprising acid groups. Even theoretically non-acidic molecular sieves typically comprise some residual acid groups introduced during preparation of the molecular sieve and/or molecular sieve-comprising catalyst. In the absence of any acid groups in the molecular sieve-comprising catalyst it may be preferred to add such groups either by treating the molecular sieve-comprising catalyst to introduce such groups essentially at the surface of the catalyst through impregnation with an acid that resides on the catalyst after calcination, for instance by treating the molecular sieve-comprising catalyst with an acid, such as phosphoric acid, or adding an acid component to catalyst formulation comprising the molecular sieve-comprising catalyst, such as alumina.

Alternatively, the oxygenate-comprising feedstock is contacted with an acid catalyst, prior to contacting the molecular sieve-comprising catalyst. This may for instance be done by passing oxygenate-comprising feedstock through an acid catalyst comprising bed or by passing the feedstock through an acid grid or filter. Preferably, the oxygenate-comprising feedstock is contacted with the acid catalyst at a temperature above 150° C. More preferably, the oxygenate-comprising feedstock is contacted with the acid catalyst at a temperature above 350° C.

Preferably, steam is present as the tert-alkyl ether contacts the catalyst. Steam is believed to increase the selectivity of the reaction.

At least part of the methanol obtained following the decomposition of the tert-alkyl ether is subsequently converted to ethylene and/or propylene over the molecular sieve-comprising catalyst under the process conditions applied. Any residual methanol in the ether-enriched stream is also converted under these conditions.

As mentioned hereinabove it is believed that upon contact with the molecular sieve-comprising catalyst, the tert-alkyl ether decomposes into methanol and an iso-olefin, e.g. isobutene or isopentene. Depending on the nature of the molecular sieve in the molecular sieve-comprising catalyst, the obtained iso-olefins are either, at least partially, converted to ethylene and/or propylene or remain unconverted.

In one preferred embodiment, at least part of the tert-alkyl ether in the ether-enriched stream is provided to step (a). In this embodiment, at least part of the ether-enriched stream is recycled to step (a), either as part of the stream comprising C4+ olefins or together with the stream comprising C4+ olefins. By recycling at least part of the ether-enriched stream to step (a), steps (a) and (f) of the process according to the invention are at least partly combined. By contacting the tert-alkyl ether with the zeolite-comprising catalyst in step (a), at least part of the ether is converted in to ethylene and propylene together with the C4+ olefins in the C4+ olefins-comprising stream. This embodiment has the advantage that only a single catalytic stage is required, although more catalytic stages may be provided, as both the conversion of the C4+ olefins and the tert-alkyl ethers is done by the same catalyst. In case, both a C4+ olefins comprising stream and an oxygenate, such as an tert-alkyl ether, are provided to step (a), step (a) may be considered as an OTO process and operated as such an OTO process. Process conditions for operating an OTO process are provided herein below. Preferably, in addition to the stream comprising C4+ olefins and tert-alkyl ethers, further oxygenates are provided to step (a) of the process. These further oxygenates may be provided as part of the stream comprising C4+ olefins, as part of the ether-enriched stream and/or separately. Preferred oxygenates to be additionally provided to step (a) include, methanol and dimethylether. In case further oxygenates, such as methanol or dimethylether, are provided to the step (a), the C4+ olefins in the stream comprising C4+ olefins may be provided solely by the recycle of C4+ olefins according to step (b) of the process, i.e. no external C4+ olefins are provided to the process. Sufficient C4+ olefins may be produced by step (a) of the process to maintain a constant recycle of C4+ olefins. However, in such a case it may be desired to provide some external C4+ olefins during start-up of the process.

In another preferred embodiment, the ether-enriched stream is provided to a separate OTO process and converted to ethylene and/or propylene by contact with a molecular sieve catalyst at a temperature in the range of from 350 to 1000°, preferably 350 to 750° C. This embodiment has the advantage that a greater degree of catalyst choice is obtained to achieve optimal conversion of the C4+ olefins in the stream comprising C4+ olefins and the tert-alkyl ethers, separately. In addition, this embodiment allows for the use of an existing OTO process to convert the tert-alkyl ethers, preferably in combination with other oxygenates, such as methanol or dimethylether. In such an embodiment, it is preferred that at least part of any C4+ olefins in the product stream of the OTO process are provided to step (a) of the process according to the invention as part of the stream comprising C4+ olefins. Step (a) of the present process may in such an embodiment act as an olefin cracking process, also referred to as OCP, used to convert at least part of the C4+ olefins in the effluent of an OTO process. Combinations of OTO processes with olefin cracking processes are well known in the art. Preferably in such a combination, (i) an oxygenate-comprising feedstock is provided to an oxygenate-to-olefin process to produce a product stream comprising ethylene and/or propylene and C4+ olefins, (ii) at least part of such C4+ olefins are provided to step (a) of the process according to the invention, as part of the stream comprising C4+ olefins, and (iii) wherein least part of the ether-enriched stream obtained in step (d) is provided to the oxygenate-to-olefin process together with or as part of the oxygenate-comprising feedstock. This embodiment is particularly preferred when the molecular sieve-comprising catalyst comprises at least one SAPO, AlPO, or MeAlPO type molecular sieve, preferably SAPO-34, as these catalysts are less suitable to convert iso-olefins.

In the process according to the invention, the stream comprising C4+ olefins may be any stream comprising C4+ olefins. C4+ olefins in the stream comprising C4+ olefins may be provided solely by the internal recycle of C4+ olefins as described herein above. The stream comprising C4+ olefins may also be an external stream. Examples of such streams may include streams comprising C4+ olefins obtained from an FCC or steam cracking process. Preferably, at least part of the stream comprising C4+ olefins is obtained from an OTO process, wherein an oxygenate-comprising feed is converted to a product stream comprising ethylene and/or propylene and comprising C4+ olefins. Preferably, the oxygenate-comprising feed is converted by contacting the feed with a molecular-sieve-comprising catalyst at a temperature in the range of from 350 to 1000° C., more preferably 350 to 700° C.

At least part of the stream comprising C4+ olefins can be obtained by separating a fraction comprising C4+ olefins from the streams obtained from e.g. an FCC, steam cracking or OTO process. This fraction comprising C4+ olefins may separated from the remainder these streams by any suitable work-up section. The design of the work-up section depends on the exact composition of the streams, and may include several separation steps.

It is particularly preferred that at least part of the stream comprising C4+ olefins is obtained from an OTO process, of which the oxygenate-comprising feed to that OTO process comprised at least part ether-enriched stream. As described herein above, feeding the tert-alkyl ethers obtained in step (c) of the process to a process wherein they are contacted with a molecular sieve-comprising catalyst at elevated temperatures may result a decomposition of the tert-alkyl ether into at least an iso-olefin, such as iso-butene and isopentene. Any unconverted iso-butene and isopentene may preferably be provided to step (a) of the process as part of the stream comprising C4+ olefins, wherein at least part of these iso-olefins are converted to ethylene and/or propylene in contact with the zeolite-comprising catalyst of step (a).

Optionally, prior to converting the ether-enriched stream to further ethylene and/or propylene, at least part of the tert-alkyl ether in the ether-enriched stream is decomposed in to methanol and an iso-olefin, and subsequently at least part of the iso-olefin is isomerised to a normal-olefin. This has the advantage that normal-olefins are more easily converted to at least ethylene and/or propylene than iso-olefins, when contacted with the molecular sieve-comprising catalyst in an OTO process. Decomposition of the tert-alkyl ether can be done by a process and catalyst as used for the original etherification, however by using a temperature above 150° C., preferably above 175° C., more preferably above 200° C., the etherification reaction is reversed.

In addition to catalyzing the decomposition of the ether, the etherification catalyst may also induce skeletal isomerisation of the resulting iso-olefin to its corresponding normal-olefin at the mentioned temperatures, although temperatures in the range of from 250 to 350° C. are preferred. Alternatively, at least part of the iso-olefins is isomerised in a separate isomerisation process. Such an isomerisation process may be any isomerisation process known for isomerising of iso-olefins to normal olefins. One such process, involves contacting the iso-olefins with a SAPO-11 molecular sieve at temperatures above 200° C.

As mentioned herein above, the purge stream still comprises normal C4+ olefins. The yield of ethylene and/or propylene may be even further increased by subjecting normal olefins in the purge stream to an isomerisation process, wherein at least part of the normal olefins are isomerised to iso-olefins. This may be done by a process similar to the process used to isomerise iso-olefins to normal olefins, as the reaction is an equilibrium reaction. The formed iso-olefins may be extracted from the purge stream for instance by providing at least part of the purge stream comprising iso-olefins back to the etherification process in step (c) of the process as part of or together with the second part of the C4+ hydrocarbon fraction. Alternatively, at least part of the purge stream comprising the newly formed iso-olefins is subjected to a separate etherification process.

In the process according to the invention, iso-olefins are reacted with methanol in an etherification process. The etherification process may be any suitable etherification process available in the art for etherifying methanol and iso-olefins to tert-alkyl ethers. Reference is made to the Handbook of MTBE and Other Gasoline Oxygenates, H. Hamid and M. A. Ali ed., 1$^{st}$ edition, Marcel Dekker, New York, 2004, pages 65 to 223, where several established process and catalyst for preparing tert-alkyl ethers such as MTBE and TAME are described. In particular reference is made to chapter 9, pages 203 to 220 of the Handbook of MTBE and Other Gasoline Oxygenates, wherein suitable commercial etherification processes are described. A preferred etherification process is an etherification process wherein the iso-olefins are converted with methanol to a tert-alkyl ether in the presence of a catalyst. Any homogeneous or heterogeneous Brönsted acid may be used to catalyze the etherification reaction. Such catalyst include: sulfuric acid, zeolites, pillared silicates, supported fluorocarbonsulphonic acid polymers and protonated cation-exchange resins catalyst, preferred catalyst are protonated cation-exchange resins catalyst due to the higher catalytic activity and the bound acid sites. A commonly used catalyst is Amberlyst 15.

Preferably, the iso-olefins are converted with methanol to a tert-alkyl ether at a temperature in the range of from 30 to 100° C., more preferably 40 to 80° C. Preferably, the iso-olefins are converted with methanol to a tert-alkyl ether at a pressures in the range of from 5 to 25 bar, more preferably 6 to 20 bar.

The iso-olefins may be converted with methanol to a tert-alkyl ether in any etherification process, however, one preferred etherification process is based on a reactive distillation, which allows for a continuous etherification and separation of the formed ethers.

The C4+ hydrocarbon fraction may comprise diolefins. Preferably, at least the part of the C4+ hydrocarbon fraction subjected to the etherification process is selectively hydrogenated to remove at least part of any diolefins, by hydrogenating the diolefins to mono-olefins and/or paraffins, preferably to mono-olefins.

In the present invention, an oxygenate feedstock, including feedstocks comprising tert-alkyl ethers, may be converted in an oxygenate-to-olefins (OTO) process. This may be any suitable OTO process known in the art in the art. Preferably, it is an OTO process in which an oxygenate feedstock is contacted in an OTO zone with an oxygenate conversion catalyst under oxygenate conversion conditions, to obtain a conversion effluent comprising lower olefins. Reference herein to an oxygenate feedstock is to an oxygenate-comprising feedstock. In the OTO zone, at least part of the feedstock is converted into a product containing one or more olefins, preferably including lower olefins, in particular ethylene and typically propylene. Preferably, the product comprises advantageously at least 50 mol %, in particular at least 50 wt %, ethylene and propylene, based on total hydrocarbon content in the product.

The oxygenate used in the process according to the invention is preferably an oxygenate which comprises at least one oxygen-bonded alkyl group. The alkyl group preferably is a C1-C5 alkyl group, more preferably C1-C4 alkyl group, i.e. comprises 1 to 5, respectively, 4 carbon atoms; more preferably the alkyl group comprises 1 or 2 carbon atoms and most preferably one carbon atom. Examples of oxygenates that can be used in the oxygenate feedstock include alcohols and ethers. Examples of preferred oxygenates include alcohols, such as methanol, ethanol, propanol; and dialkyl ethers, such as dimethylether, diethylether, methylethylether. Preferably, the oxygenate is methanol or dimethylether, or a mixture thereof.

In the process according to the invention, it is preferred that the oxygenate feedstock also includes a tert-alkyl ether produced by step (c) of the process according to the invention.

Preferably the oxygenate feedstock comprises at least 50 wt % of oxygenate, in particular methanol and/or dimethylether, based on the total of hydrocarbons and oxygenates in the oxygenate feedstock, more preferably at least 70 wt %.

The oxygenate feedstock can comprise an amount of diluents. During the conversion of the oxygenates, steam is produced as a by-product, which serves as an in-situ produced diluent. Optionally additional steam is added as diluent. The amount of additional diluent that needs to be added depends on the in-situ water make, which in turn depends on the composition of the oxygenate-comprising feed. Where methanol produces 1 mol of water per mol of carbon atoms supplied to the process, MTBE, for example only produces 0.20 mol of water per 1 mol of carbon atoms supplied to the process. Where the diluent is water or steam, the molar ratio of oxygenate to diluent is between 10:1 and 1:20. In case, the oxygenate-comprising feedstock comprises in the range of from 0.01 to 50 wt %, preferably of from 1 to 10 wt %, of tert-alkyl ether, based on the oxygenates in the oxygenate-comprising feedstock, the molar ratio of oxygenate to diluent is preferably in the range of from 3:1 to 1:5, preferably 2:1 to 1:2. In case, the oxygenate-comprising feedstock comprises in the range of from 50 to 100 wt %, preferably 60 to 95 wt %, of tert-alkyl ether, based on the oxygenates in the oxygenate-comprising feedstock, the molar ratio of oxygenate to diluent is preferably in the range of from 1:3 to 1:15, preferably 1:4 to 1:10.

Due to the low in-situ water make of tert-alkyl ethers, the use of diluents other than water may be preferred, in particular when the catalyst is sensitive to hydrothermal deactivation. Other suitable diluents include inert gases such as nitrogen, but may also include paraffins.

Preferably, in addition to the oxygenate, an olefinic co-feed is provided along with and/or as part of the oxygenate feedstock to the OTO process. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species.

Preferably, at least 70 wt % of the olefinic co-feed, during normal operation, is formed by a recycle stream of a C3+ or C4+ hydrocarbon fraction from the OTO conversion effluent, preferably at least 90 wt % of olefinic co-feed, based on the whole olefinic co-feed, is formed by such recycle stream. In order to maximize production of ethylene and propylene, it is desirable to maximize the recycle of C4 olefins in the effluent of the OTO process. This can be done by recycling at least part of the C4+ hydrocarbon fraction, preferably C4-C5 hydrocarbon fraction, more preferably C4 hydrocarbon fraction, in the OTO effluent. However, a certain part thereof, such as between 1 and 5 wt %, needs to be withdrawn as purge, since otherwise saturated hydrocarbons, in particular C4's (butane) would build up in the process, which are substantially not converted under the OTO reaction conditions.

The preferred molar ratio of oxygenate in the oxygenate feedstock to olefin in the olefinic co-feed provided to the OTO conversion zone depends on the specific oxygenate used and the number of reactive oxygen-bonded alkyl groups therein. Preferably the molar ratio of oxygenate to olefin in the total feed, i.e. oxygenate feedstock and olefinic co-feed, lies in the range of 20:1 to 1:10, more preferably in the range of 18:1 to 1:5, still more preferably in the range of 15:1 to 1:3, even still more preferably in the range of 12:1 to 1:3. For purposes of calculating the molar ratio of oxygenate to olefin in the total feed, the olefins provided to the process as part of the tert-alkyl ether must also be taken into account.

A variety of OTO processes is known for converting oxygenates such as for instance methanol or dimethylether to an olefin-containing product, as already referred to above. One such process is described in WO A 2006/020083. Processes integrating the production of oxygenates from synthesis gas and their conversion to light olefins are described in US20070203380A1 and US20070155999A1.

In the process according to the present invention two types of catalyst are used, i.e. molecular sieve-comprising catalyst and zeolite-comprising catalyst. Such catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing [TO4] tetrahedral units, more preferably, two or more [SiO4], [AlO4] and/or [PO4] tetrahedral units. These silicon, aluminum and/or phosphorous based molecular sieves and metal containing silicon, aluminum and/or phosphorous based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminiophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

A particular class of molecular sieves are zeolites. Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Zeolites are preferred when the feedstock to be converted comprises olefins, e.g. in step (a).

Zeolite-comprising catalysts are known for their ability to convert higher olefins to lower olefins, in particular C4+ olefins to ethylene and/or propylene. Particular preferred zeolite-comprising catalyst for converting higher olefins to lower olefins, and in particular converting at least part of the stream comprising C4+ olefins to the olefinic product in step (a), are catalysts comprising at least one zeolite selected from MFI, MEL, TON and MTT type zeolites, more preferably at least one of ZSM-5, ZSM-11, ZSM-22 and ZSM-23 zeolites. In addition to the above described conversion of higher olefins to lower olefins, the zeolite-comprising catalyst have the additional advantage that these catalysts are also suitable for converting oxygenates to lower olefins, in particular ethylene and/or propylene. As a result, when, as described above, a tert-alkyl ether is contacted with such catalyst under the described process conditions, the tert-alkyl ether is decomposed into methanol or ethanol and the corresponding iso-olefin, which may both be converted into ethylene and/or propylene. As zeolites are a type of molecular sieves, references herein to molecular sieve-comprising catalysts include zeolite-comprising catalysts.

In one preferred embodiment, the catalysts of step (a) and step (f) are the same zeolite-comprising catalyst and at least part of the tert-alkyl ether is recycled to step (a), by providing at least part of the ether-enriched stream to step (a).

In another preferred embodiment, the catalyst of step (f) is a non-zeolitic molecular sieve-comprising catalyst. In this embodiment, the further olefinic product obtained in step (f) by contacting the ether-enriched stream with the non-zeolitic molecular sieve-comprising catalyst, is at least in part provided to step (a). At least part of any C4+ olefins in the further olefinic product may be converted to at least ethylene and/or propylene in contact with the zeolite-comprising molecular sieve of step (a).

Preferred catalysts, for both step (a) as well as step (f), comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80. The oxygenate conversion catalyst can comprise at least 1 wt %, based on total molecular sieve in the oxygenate conversion catalyst, of the second molecular sieve having more-dimensional channels, preferably at least 5 wt %, more preferably at least 8 wt %.

Particular preferred catalyst, for both step (a) as well as step (f), include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50% wt of such zeolites based on total zeolites in the catalyst.

In a particularly preferred embodiment for both step (a) as well as step (f), the catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11. Such further zeolite (molecular sieve) can have a beneficial effect on the stability of the catalyst in the course of the process and under hydrothermal conditions.

The catalyst for both step (a) as well as step (f) may comprise phosphorous as such or in a compound, i.e. phosphorous other than any phosphorous included in the framework of the molecular sieve. It is preferred that an MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorous as such or in a compound in an elemental amount of from 0.05 to 10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

It is preferred that zeolites and respectively molecular sieves in the hydrogen form are used in the catalyst for both step (a) and (f), e.g., HZSM-22, HZSM-23, and HZSM-48, HZSM-5. Preferably at least 50 wt %, more preferably at least 90 wt %, still more preferably at least 95 wt % and most preferably 100 wt % of the total amount of molecular sieve used is in the hydrogen form. It is well known in the art how to produce such molecular sieves in the hydrogen form.

The reaction conditions of the oxygenate conversion include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Typically the catalyst deactivates in the course of the process, primarily due to deposition of coke on the catalyst. The phenomenon is typically observed in both step (a) as well as in step (f) of the process. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 µm, preferably 50-100 µm.

Step (a) of the process may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

Step (f) of the process may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

In step (a) of the process an olefinic product stream comprising ethylene and/or propylene is retrieved. As described herein above, at least part of the tert-alkyl ether in the ether-enriched stream is converted in step (f) to a further olefinic product stream comprising ethylene/and propylene. The ethylene and/or propylene may be separated from the remainder of the components in the olefinic product and further olefinic product. Preferably the olefinic product and further olefinic product at least partially, and preferably fully, combined prior to separating the ethylene and/or propylene from the remaining components. Where the olefinic product comprises ethylene, least part of the ethylene may be further converted into at least one of polyethylene, mono-ethylene-glycol, ethylbenzene and styrene monomer. Where the olefinic product comprises propylene, at least part of the propylene may be further converted into at least one of polypropylene and propylene oxide.

In the process according to the invention at least part of tert-alkyl ethers are converted to ethylene and/or propylene. Optionally, another part of the tert-alkyl ethers are exported from the process as products, e.g. MTBE and/or TAME. Such ethers are suitably used as fuel additives.

DETAILED DESCRIPTION OF THE DRAWINGS

In FIG. 1, a process according to the present invention is schematically represented, wherein the tert-alkyl ether comprised in the ether-enriched stream is converted together with the stream comprising C4+ olefins in contact with an zeolite-comprising catalyst in reaction zone 5. In FIG. 1, stream 1 comprising C4+ olefins is provided to reactor zone 5. In reactor zone 5, stream 1 is contacted with a zeolite comprising catalyst, for example a catalyst comprising ZSM-5, such as a catalyst comprising 50 wt % of ZSM-5 and 50 wt % ZSM-23, based on the zeolite content in the catalyst. Olefinic product stream 10 is retrieved from reactor zone 5 and provided to separation zone 15. Separation zone 15 may for instance include a quench tower set for receiving olefinic product stream 10. In the quench tower high boiling components such as water may be removed, the remaining stream may be compressed in a multi stage compressor zone, with interstage cooling and separation of condensed phases. The compressed vapour stream may be provided to a combination of a de-ethaniser and a de-propaniser to separate the compressed vapour stream into at least ethylene and/or propylene and a C4+ hydrocarbon fraction. The ethylene and/or propylene may be retrieved from separation zone 15 separately or as a mixture via one or more streams 20. C4+ hydrocarbon fraction 25 is retrieved from separation zone 15. Part of C4+ hydrocarbon fraction 25a is recycled to reactor zone 5. Second part of C4+ hydrocarbon fraction 25b is provided to etherification zone 30, together with methanol 35. In etherification zone 30, C4+ hydrocarbon fraction 25b is contacted with methanol 35 over an etherification catalyst, such as for instance a protonated cationic-exchange resin. Etherification product 40 is retrieved from etherification zone 30 and provided to second separation zone 45, wherein etherification product 40 is separated into an ether-enriched stream 50 and an iso-olefin-depleted stream 55. Optionally, zones 30 and 45 are combined into a reactive distillation zone, wherein iso-olefins are reacted with methanol to tert-alkyl ethers, while continuously separating tert-alkyl ether from the reaction mixture. Optionally, zones 30 and 45 allow for the recycle of part of the iso-olefin depleted stream in case not all of the iso-olefins are converted to tert-alkyl ether in a single pass process. Ether-enriched stream 50 is combined with stream 1, while iso-olefin-depleted stream 55 purged from the process. Optionally, additional oxygenate (not shown), such as methanol or dimethylether, and water is added to reactor zone 5.

In FIG. 2, a process according to the present invention is schematically represented, wherein the tert-alkyl ether comprised in the ether-enriched stream is converted separately in an OTO process and reaction zone 5 is operated as an OCP zone. In FIG. 2, stream 1 comprising C4+ olefins is provided to reactor zone 5. In reactor zone 5, stream 1 is contacted with a zeolite comprising catalyst, for example a catalyst comprising ZSM-5, such as a catalyst comprising 50 wt % of ZSM-5 and 50 wt % ZSM-23, based on the zeolite content in the catalyst. Olefinic product stream 10 is retrieved from reactor zone 5 and provided to separation zone 215, Separation zone 215 may be similar to separation zone 15 described herein above, however the presence of a quench tower is optional depending on the concentration of water vapour in olefinic product stream 10. Ethylene and/or propylene may be retrieved from separation zone 215 separately or as a mixture via one or more streams 20. C4+ hydrocarbon fraction 25 is retrieved from separation zone 215. Part of C4+ hydrocarbon fraction 25a is recycled to reactor zone 5. Second part of C4+ hydrocarbon fraction 25b is provided to etherification zone 30, together with methanol 35. In etherification zone 30, C4+ hydrocarbon fraction 25b is contacted with methanol 35 over an etherification catalyst, such as for instance a protonated cationic-exchange resin. Etherification product 40 is retrieved from etherification zone 30 and provided to second separation zone 45, wherein etherification product 40 is separated into an ether-enriched stream 50 and an iso-olefin-depleted stream 55. Optionally, zones 30 and 45 are combined into a reactive distillation zone, wherein iso-olefins are reacted with methanol to tert-alkyl ethers, while continuously separating tert-alkyl ether from the reaction mixture. Optionally, zones 30 and 45 allow for the recycle of part of the iso-olefin depleted stream in case not all of the iso-olefins are converted to tert-alkyl ether in a single pass process. Iso-olefin-depleted stream 55 is withdrawn from process as purge stream. Ether-enriched stream 50 is provided to oxygenate-to-olefin zone 200. In oxygenate-to-olefin zone 200, ether-enriched stream 50 is contacted with a molecular sieve-comprising catalyst, for example a catalyst comprising ZSM-5, such as a catalyst comprising 50 wt % of ZSM-5 and 50 wt % ZSM-23, based on the zeolite content in the catalyst, or a catalyst comprising SAPO-34. Optionally, additional oxygenate, such as methanol or dimethylether, olefins and water are added to oxygenate-to-olefin zone 200 via conduit 205. Product stream 210 is retrieved from oxygenate-to-olefin zone 200 and provided to third separation zone 220, which may be a separation zone similar to separation zone 15, described hereinabove. From third separation zone 220, ethylene and/or propylene may be retrieved separately or as a mixture via one or more streams 225. C4+ hydrocarbon fraction 230 is retrieved from third separation zone 220 and provided to reaction zone 5 as stream 1.

In FIG. 3, a process according to the present invention similar to that in FIG. 2 is schematically represented, wherein separation section 215 and 220 are integrated.

In FIG. 3, a stream comprising C4+ olefins is provided to reactor zone 5. In reactor zone 5, the stream comprising C4+ olefins is contacted with a zeolite comprising catalyst, for example a catalyst comprising ZSM-5, such as a catalyst comprising 50 wt % of ZSM-5 and 50 wt % ZSM-23, based on the zeolite content in the catalyst. Olefinic product stream 10 is retrieved from reactor zone 5 and provided to separation zone 315, Separation zone 315 may be similar to separation zone 15 described herein above. Olefinic product stream 10 may be provided to separation zone 315 before or after the quench tower depending on the concentration of water vapour in olefinic product stream 10.

An oxygenate-comprising stream is provided to oxygenate-to-olefin zone 200. In oxygenate-to-olefin zone 200, the oxygenate-comprising stream is contacted with a molecular sieve-comprising catalyst, for example a catalyst comprising ZSM-5, such as a catalyst comprising 50 wt % of ZSM-5 and 50 wt % ZSM-23, based on the zeolite content in the catalyst, or a catalyst comprising SAPO-34. Product stream 210 is retrieved from oxygenate-to-olefin zone 200 and provided to separation zone 315, preferably such that is provided before the quench tower.

Ethylene and/or propylene may be retrieved from separation zone 315 separately or as a mixture via one or more streams 20. C4+ hydrocarbon fraction 25 is retrieved from separation zone 315. Part of C4+ hydrocarbon fraction 25a is recycled to reactor zone 5. Second part of C4+ hydrocarbon fraction 25b is and provided to etherification zone 30, together with methanol 35. In etherification zone 30, C4+ hydrocarbon fraction 25b is contacted with methanol 35 over an etherification catalyst, such as for instance a protonated cationic-exchange resin. Etherification product 40 is retrieved from etherification zone 30 and provided to second separation zone 45, wherein etherification product 40 is separated into an ether-enriched stream 50 and an iso-olefin-depleted stream 55. Optionally, zones 30 and 45 are combined into a reactive distillation zone, wherein iso-olefins are reacted with methanol to tert-alkyl ethers, while continuously separating tert-alkyl ether from the reaction mixture. Optionally, zones 30 and 45 allow for the recycle of part of the iso-olefin depleted stream in case not all of the iso-olefins are converted to tert-alkyl ether in a single pass process. Iso-olefin-depleted stream 55 is withdrawn from process as purge stream. Ether-enriched stream 50 is provided to oxygenate-to-olefin zone 200 as, at least part of, the oxygenate comprising stream to oxygenate-to-olefin zone 200. Optionally, additional oxygenate, such as methanol or dimethylether, olefins and water are added to form part of the oxygenate-comprising stream to oxygenate-to-olefin zone 200 via conduit 205.

EXAMPLES

The invention is illustrated by the following non-limiting examples.

Example 1

Several molecular sieves were tested to show their ability to convert MTBE to an olefinic product. To test the molecular sieves for catalytic performance, a powder of the respective molecular sieves was pressed into tablets and the tablets were broken into pieces and sieved. MTBE was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the reaction temperature and a mixture consisting of 6 vol % MTBE balanced in $N_2$ was passed over the catalyst at atmospheric pressure (1 bar). The Gas Hourly Space Velocity (GHSV) is determined by the total gas flow over the zeolite weight per unit time (ml·gzeolite$^{-1}$·h$^{-1}$). The gas hourly space velocity used in the experiments was 10000 (ml·gzeolite$^{-1}$·h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The effluent from the reactor obtained at several reactor temperatures was analyzed. The results are shown in Table 1.

For all tested catalyst, the conversion of MTBE was complete. No MTBE or methanol was detected in the effluent of the reactor.

The zeolite catalysts, i.e. ZSM-5, ZSM-22 and ZSM-23, show a good conversion of the MTBE, including the isobutene part of the MTBE, to ethylene and propylene. An advantage of the one-dimensional zeolites having 10-membered ring channels, i.e. ZSM-22 and ZSM-23, is the lower paraffin make and C6+ make compared to the multi-dimensional ZSM5 zeolites.

By reducing the SAR of the ZSM-5 catalyst, the ethylene and propylene yield is improved, while significantly less C4 olefins are produced.

The non-zeolite SAPO-34 catalyst shows a low paraffin make and C6+ make, however is less suitable for converting iso-C4 olefins as can be seen from the relative high C4 olefin content in the effluent of the reactor. These C4 olefins are preferably subsequently converted in an OCP reactor over a zeolite catalyst. It will be clear from table 2, that zeolite catalyst show a better conversion of C4 olefins to the desired ethylene and propylene products. Increasing the reaction temperature, results in a reduction of the C4 olefin content in the effluent of the reaction.

Example 2

Several molecular sieves were tested to show their ability to convert a mixture of MTBE and methanol to an olefinic product. To test the molecular sieves for catalytic performance, a powder of the respective molecular sieves was pressed into tablets and the tablets were broken into pieces and sieved. A mixture of MTBE and methanol was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to 525° C. and a mixture consisting of 3 vol % MTBE and 3 vol % methanol, balanced in $N_2$ was passed over the catalyst at atmospheric pressure (1 bar). The Gas Hourly Space Velocity (GHSV) is determined by the total gas flow over the zeolite weight per unit time (ml·gzeolite$^{-1}$·h$^{-1}$). The gas hourly space velocity used in the experiments was 10000 (ml·gzeolite$^{-1}$·h$^{-1}$). The effluent from the reactor was analyzed by gas chromatography (GC) to determine the product composition. The composition has been calculated on a

TABLE 1

| T [° C.] | Catalyst | C2= [wt %] | C3= [wt %] | C4= [wt %] | C5 [wt %] | Light ends [wt %] | C6+ [wt %] | C4 paraffin [wt %] |
|---|---|---|---|---|---|---|---|---|
| 420 | SAPO-34 | 7.90 | 15.15 | 65.43 | 9.18 | 0.19 | 1.06 | 1.09 |
| 525 | SAPO-34 | 9.41 | 18.17 | 50.01 | 14.78 | 1.57 | 2.58 | 3.49 |
| 420 | ZSM-5* | 10.86 | 28.10 | 15.93 | 8.13 | 0.12 | 23.56 | 13.31 |
| 525 | ZSM-5* | 26.77 | 38.11 | 11.46 | 2.69 | 0.03 | 13.01 | 7.92 |
| 525 | ZSM-5# | 17.89 | 39.85 | 25.49 | 3.22 | 1.79 | 9.69 | 2.07 |
| 525 | ZSM-23 | 20.73 | 42.89 | 29.00 | 2.05 | 0.59 | 3.62 | 1.12 |
| 525 | ZSM-22 | 17.19 | 39.88 | 35.52 | 2.12 | 0.44 | 3.99 | 0.86 |

*SAR 80
SAR 280 weight basis of all hydrocarbons analyzed. The composition has been defined by the division of the mass of a specific product by the sum of the masses of all products. The results are shown in Table 2.

TABLE 2

| T [° C.] | Catalyst | C2 = [wt %] | C3 = [wt %] | C4 = [wt %] | C5 [wt %] | Light ends [wt %] | C6 + [wt %] | C4 paraffin [wt %] |
|---|---|---|---|---|---|---|---|---|
| 525 | SAPO-34 | 18.11 | 22.08 | 44.94 | 8.23 | 2.94 | 1.64 | 2.05 |
| 525 | ZSM-5* | 25.72 | 37.64 | 11.57 | 3.24 | 0.65 | 13.79 | 7.41 |
| 525 | ZSM-5# | 17.66 | 42.42 | 20.31 | 3.31 | 1.82 | 12.88 | 1.61 |
| 525 | ZSM-23 | 21.45 | 46.66 | 21.09 | 2.77 | 0.81 | 6.16 | 1.06 |
| 525 | ZSM-22 | 17.84 | 48.46 | 24.30 | 2.61 | 0.83 | 5.24 | 0.71 |

*SAR 80
SAR 280

The zeolite catalysts do not show a significant change in the obtained C2 to C4 olefinic product slate, when methanol is added to the MTBE feed. As a result, it can be expected that for an existing methanol based OTO process using a zeolite catalyst, MTBE can be blended into the methanol feed without requiring significant changes to the process operation. In case of the SAPO-34 catalyst, the ratio of propylene to ethylene obtained when using only MTBE as a feed is higher than the ratio obtained from a feed comprising a mixture of MTBE and methanol. As a result it can be concluded that blending MTBE into a methanol feedstock to a SAPO-34 based OTO process may result in an improved ratio of propylene to ethylene without requiring significant changes to the process operation.

What is claimed is:

1. A process for preparing ethylene and/or propylene, comprising the steps of:
   a) contacting a stream comprising C4+ olefins with a zeolite-comprising catalyst at a temperature in the range of from 350 to 1000° C. and retrieving an olefinic product stream comprising:
      ethylene and/or propylene, and
      a C4+ hydrocarbon fraction, comprising paraffins, normal olefins and iso-olefins;
   a1) dividing the C4+ hydrocarbon fraction into a first part and a second part;
   b) recycling a first part of the C4+ hydrocarbon fraction to step (a);
   c) subjecting a second part of the C4+ hydrocarbon fraction to an etherification process with methanol and/or ethanol wherein at least part of the iso-olefins are converted with methanol and/or ethanol to an tert-alkyl ether, and retrieving an etherification product stream;
   d) separating at least part of the etherification product stream into at least an ether-enriched stream and an iso-olefin-depleted C4+ hydrocarbon stream;
   e) withdrawing at least part of the iso-olefin-depleted C4+ hydrocarbon stream from the process to purge part of the paraffinic C4+ hydrocarbons;
   f) converting at least part of the tert-alkyl ether in the ether-enriched stream to ethylene and/or propylene by contacting at least part of the ether-enriched stream with a molecular sieve-comprising catalyst at a temperature in the range of from 350 to 1000° C.

2. A process according to claim 1, wherein step (f) comprises recycling at least part of the ether-enriched stream to step (a).

3. A process according to claim 1, further comprising providing an oxygenate-comprising stream to step (a) and contacting the oxygenate-comprising stream with the zeolite-comprising catalyst together with the C4+ olefins.

4. A process according to claim 1, wherein part of the stream comprising C4+ olefins is obtained by converting an oxygenate-comprising feed to a product stream comprising:
   ethylene and/or propylene, and —C4+ olefins.

5. A process according to claim 4, wherein the oxygenate-comprising feed is converted by contacting the oxygenate-comprising feed with a molecular sieve-comprising catalyst at a temperature in the range of from 350 to 1000° C.

6. A process according to claim 5, wherein the oxygenate-comprising feed comprises at least part of the ether-enriched stream.

7. A process according to claim 4, wherein the molecular sieve-comprising catalyst comprises at least one SAPO, AlPO, or MeAlPO type molecular sieve.

8. A process according to claim 1, wherein the zeolite-comprising catalyst comprises at least one zeolite selected from MFI, MEL, TON and MTT type zeolites.

9. A process according to claim 1, wherein the iso-olefins include at least one of isobutene and isopentene.

10. A process according to claim 1, wherein the iso-olefins are converted with methanol to the tert-alkyl ether by contacting the iso-olefin with methanol in the presence of an etherification catalyst at a temperature in the range of from 30 to 100° C.

11. A process according to claim 10, wherein the etherification catalyst is a protonated cation-exchange resin catalyst.

12. A process according to claim 1, wherein an oxygenate-comprising feedstock is provided to an oxygenate-to-olefin process to produce a product stream comprising ethylene and/or propylene and C4+ olefins, at least part of which C4+ olefins are provided to step (a) of the process according to any one of claims 1 to 11, as part of the stream comprising C4+ olefins and wherein least part of the ether-enriched stream obtained in step (e) is provided to the oxygenate-to-olefin process together with or as part of the oxygenate-comprising feedstock.

13. A process according to claim 1, wherein the olefinic product comprises ethylene and at least part of the ethylene is further converted into at least one of polyethylene, mono-ethylene-glycol, ethylbenzene and styrene monomer.

14. A process according to claim 1, wherein the olefinic product comprises propylene and at least part of the propylene is further converted into at least one of polypropylene and propylene oxide.

* * * * *